(12) United States Patent
Hawkins

(10) Patent No.: US 6,288,246 B1
(45) Date of Patent: Sep. 11, 2001

(54) PROCESS FOR PREPARING HYDROXAMIC ACIDS

(75) Inventor: Joel M. Hawkins, Old Lyme, CT (US)

(73) Assignee: Pfizer Inc, New York, NY (US)

( * ) Notice: Subject to any disclaimer, the term of this patent is extended or adjusted under 35 U.S.C. 154(b) by 0 days.

(21) Appl. No.: 09/287,508

(22) Filed: Apr. 7, 1999

Related U.S. Application Data

(60) Provisional application No. 60/081,365, filed on Apr. 10, 1998.

(51) Int. Cl.$^7$ .................. C07C 239/14; C07C 239/16; C07C 259/06; C07C 259/10; C07D 311/94
(52) U.S. Cl. ............................. 549/397; 564/301
(58) Field of Search .............. 549/397; 564/80, 564/95, 142, 301

(56) References Cited

U.S. PATENT DOCUMENTS 4,745,124   5/1988   Ryan et al. .

FOREIGN PATENT DOCUMENTS

| 0895988 | 2/1999 | (EP) . |
|---|---|---|
| WO 91/10644 | 7/1991 | (WO) . |
| WO 96/27583A | 9/1996 | (WO) . |
| WO 98/07697A | 2/1998 | (WO) . |
| WO 98/33768 | 8/1998 | (WO) . |
| WO 99/07675 | 2/1999 | (WO) . |
| WO 99/52910 | 10/1999 | (WO) . |

OTHER PUBLICATIONS

J.C. Bottaro et al, "Expedient Synthesis of Mono–trimethylsilyl Hydroxylamine and Bis–trimethylsilylamine", *Synthetic Communications*, vol. 15(14), pp. 1333–1335, 1985.

E. Lee, et al, "Azacycle Synthesis via Radical Cyclization of beta Aminoacrylates" *Tetrahedron Letters*, vol. 36 No. 3, Jan. 16, 1995, pp. 417–420.

Montserrat Faja, et al., "Reaction of Uridines and Thymidines with Methyl Propynoate. A New N–3 Protecting Group" *Tetrahedron Letters*, vol. 36, No. 18, pp. 3261–3264, 1995.

Tamejiro Hiyama, et al., "A New Synthesis of 3–amino–2–alkenoates. Novel Synthetic Route to Amino Sugars N–Benzoyl–L–daunosamine and L–acosamine" *Bull. Chem. Soc. Jpn.* 60, pp. 2127–2137 (Jun. 1987).

Theodora W. Greene, et al., "Protective Groups In Organic Synthesis", $2^{nd}$ edition, pp. 250–252, John Wiley & Sons, New York, 1991.

A. Burchardt, et al. "N–Substituierte 2–Aryl–2–hydroxycarbohydroxamsaurene" *Arch. Pharm* (Weinheim) 323 (3) (1990): 181–183.

A. Burchardt, et al. "Ergiebige Synthese N–substituierter Arylglyoxylohydroxamsauren" *Arch. Pharm* (Weinheim) 321 (5) (1988) pp. 311–312.

*Primary Examiner*—T. A Solola
(74) *Attorney, Agent, or Firm*—Peter C. Richardson; Paul H. Ginsburg; E. Victor Donahue

(57) ABSTRACT

The present invention relates to a process for preparing hydroxamic acids from hydroxylic acid intermediates wherein the carboxylic acid intermediate does not possess reactive substituents such as hydroxy or amino groups.

7 Claims, No Drawings

PROCESS FOR PREPARING HYDROXAMIC ACIDS

The present application claims priority under 35 USC section 119(e) to U.S. provisional application No. 60/081,365 filed Apr. 10, 1998, the complete disclosure of which is incorporated by reference as if fully set forth herein.

BACKGROUND OF THE INVENTION

The present invention relates to a process for preparing hydroxamic acids from carboxylic acid intermediates, wherein the carboxylic acid intermediate does not possess reactive substituents such as hydroxy or amino groups.

Inhibitors of matrix metalloproteinase (MMP) are known to be useful for the treatment of a condition selected from the group consisting of arthritis (including osteoarthritis and rheumatoid arthritis), inflammatory bowel disease, Crohn's disease, emphysema, acute respiratory distress syndrome, asthma, chronic obstructive pulmonary disease, Alzheimer's disease, organ transplant toxicity, cachexia, allergic reactions, allergic contact hypersensitivity, cancer, tissue ulceration, restenosis, periodontal disease, epidermolysis bullosa, osteoporosis, loosening of artificial joint implants, atherosclerosis (including atherosclerotic plaque rupture), aortic aneurysm (including abdominal aortic aneurysm and brain aortic aneurysm), congestive heart failure, myocardial infarction, stroke, cerebral ischemia, head trauma, spinal cord injury, neuro-degenerative disorders (acute and chronic), autoimmune disorders, Huntington's disease, Parkinson's disease, migraine, depression, peripheral neuropathy, pain, cerebral amyloid angiopathy, nootropic or cognition enhancement, amyotrophic lateral sclerosis, multiple sclerosis, ocular angiogenesis, corneal injury, macular degeneration, abnormal wound healing, burns, diabetes, tumor invasion, tumor growth, tumor metastasis, corneal scarring, scleritis, AIDS, sepsis, septic shock and other diseases characterized by inhibition of metalloproteinase or ADAM (including TNF-α) expression. In addition, the products which can be prepared from the compounds and processes of the present invention may be used in combination therapy with standard non-steroidal anti-inflammatory drugs (hereinafter NSAID'S), COX-2 inhibitors and analgesics for the treatment of arthritis, and in combination with cytotoxic drugs such as adriamycin, daunomycin, cis-platinum, etoposide, taxol, taxotere and alkaloids, such as vincristine, in the treatment of cancer.

Matrix metalloproteinase inhibitors are well known in the literature. Specifically, PCT publication WO 96/33172 published Oct. 24, 1996, refers to cyclic arylsulfonylamiro hydroxamic acids that are useful as MMP inhibitors. U.S. Pat. No. 5,672,615, PCT Publication WO 97/20824, PCT Publication WO 98/08825, PCT Publication WO 98/27069, and PCT Publication WO 98/34918, published Aug. 13, 1998, entitled "Arylsulfonyl Hydroxamic Acid Derivatives" all refer to cyclic hydroxamic acids that are useful as MMP inhibitors. PCT Publications WO 96/27583 and WO 98/07697, published Mar. 7, 1996 and Feb. 26, 1998, respectively, refer to arylsulfonyl hydroxamic acids. PCT Publication W/O 98/03516, published Jan. 29, 1998 refers to phosphinates with MMP activity. PCT Publication WO 98/34915, published Aug. 13, 1998, entitled "N-Hydroxy-β-Sulfonyl Propionamide Derivatives," refers to propionyl-hydroxamides as useful MMP inhibitors. PCT Publication WO 98/33768, published Aug. 6, 1998, entitled "Arylsulfonylamino Hydroxamic Acid Derivatives," refers to N-unsubstituted arylsulfonylamino hydroxamic acids. PCT Publication WO 98/30566, published Jul. 16, 1998, entitled "Cyclic Sulfone Derivatives," refers to cyclic sulfone hydroxamic acids as MMP inhibitors. U.S. Provisional Patent Application No. 60/55208, filed Aug. 8, 1997, refers to biaryl hydroxamic acids as MMP inhibitors. U.S. Provisional Patent Application Serial No. 60/55207, filed Aug. 8, 1997, entitled "Aryloxyarylsulfonylamino Hydroxamic Acid Derivatives," refers to aryloxyarylsulfonyl hydroxamic acids as MMP inhibitors. Each of the above referenced publications and applications is hereby incorporated by reference in its entirety.

SUMMARY OF THE INVENTION

The present invention relates to a process for preparing a molecule containing a hydroxamic acid group, comprising reacting hydroxylamine, or a salt thereof, with a (($C_1$–$C_6$)alkyl)$_3$silyl halide, preferably (($C_1$–$C_6$)alkyl)$_3$silyl chloride, in the presence of a base, followed by reaction with a carboxylic acid halide containing molecule followed by reaction with an acid, with the proviso that the carboxylic acid halide containing molecule does not contain a hydroxy, primary amine, secondary amine or thiol group.

The present invention relates to a process for preparing a compound of the formula

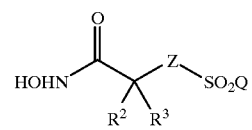

I

Z is >$CH_2$ or >$NR^1$;

Q is ($C_1$–$C_6$)alkyl, ($C_6$–$C_{10}$)aryl, ($C_2$–$C_9$)heteroaryl, ($C_6$–$C_{10}$)aryloxy($C_1$–$C_6$)alkyl, ($C_6$–$C_{10}$)aryloxy($C_6$–$C_{10}$)aryl, ($C_6$–$C_{10}$)aryloxy($C_2$–$C_9$)heteroaryl, ($C_6$–$C_{10}$)aryl($C_1$–$C_6$)alkyl, ($C_6$–$C_{10}$)aryl($C_6$–$C_{10}$)aryl, ($C_6$–$C_{10}$)aryl($C_2$–$C_9$)heteroaryl, ($C_6$–$C_{10}$)aryl($C_6$–$C_{10}$)aryl($C_1$–$C_6$)alkyl, ($C_6$–$C_{10}$)aryl($C_6$–$C_{10}$)aryl($C_6$–$C_{10}$)aryl, ($C_6$–$C_{10}$)aryl($C_6$–$C_{10}$)aryl($C_2$–$C_9$)heteroaryl, ($C_2$–$C_9$)heteroaryl($C_1$–$C_6$)alkyl, ($C_2$–$C_9$)heteroaryl($C_6$–$C_{10}$)aryl, ($C_2$–$C_9$)heteroaryl($C_2$–$C_9$)heteroaryl, ($C_6$–$C_{10}$)aryl($C_1$–$C_6$)alkoxy($C_1$–$C_6$)alkyl, ($C_6$–$C_{10}$)aryl($C_1$–$C_6$)alkoxy($C_6$–$C_{10}$)aryl, ($C_6$–$C_{10}$)aryl($C_1$–$C_6$)alkoxy($C_2$–$C_9$)heteroaryl, ($C_2$–$C_9$)heteroaryloxy($C_1$–$C_6$)alkyl, ($C_2$–$C_9$)heteroaryloxy($C_6$–$C_{10}$)aryl, ($C_2$–$C_9$)heteroaryloxy($C_2$–$C_9$)heteroaryl, ($C_2$–$C_9$)heteroaryl($C_1$–$C_6$)alkoxy($C_1$–$C_6$)alkyl, ($C_2$–$C_9$)heteroaryl($C_1$–$C_6$)alkoxy($C_6$–$C_{10}$)aryl or ($C_2$–$C_9$)heteroaryl($C_1$–$C_6$)alkoxy($C_2$–$C_9$)heteroaryl;

wherein each ($C_6$–$C_{10}$)aryl or ($C_2$–$C_9$)heteroaryl moieties of said ($C_6$–$C_{10}$)aryl, ($C_2$–$C_9$)heteroaryl, ($C_6$–$C_{10}$)aryloxy($C_1$–$C_6$)alkyl, ($C_6$–$C_{10}$)aryloxy($C_6$–$C_{10}$)aryl, ($C_6$–$C_{10}$)aryloxy($C_2$–$C_9$)heteroaryl, ($C_6$–$C_{10}$)aryl($C_1$–$C_6$)alkyl, ($C_6$–$C_{10}$)aryl($C_6$–$C_{10}$)aryl, ($C_6$–$C_{10}$)aryl($C_2$–$C_9$)heteroaryl, ($C_6$–$C_{10}$)aryl($C_6$–$C_{10}$)aryl($C_1$–$C_6$)alkyl, ($C_6$–$C_{10}$)aryl($C_6$–$C_{10}$)aryl($C_6$–$C_{10}$)aryl, ($C_6$–$C_{10}$)aryl($C_6$$C_{10}$)aryl($C_2$–$C_9$)heteroaryl, ($C_2$–$C_9$)heteroaryl($C_1$–$C_6$)alkyl, ($C_2$–$C_9$)heteroaryl($C_6$–$C_{10}$)aryl, ($C_2$–$C_9$)heteroaryl($C_2$–$C_9$)heteroaryl, ($C_6$–$C_{10}$)aryl($C_6$–$C_{10}$)aryl($C_1$–$C_6$)alkoxy($C_1$–$C_6$)alkyl, ($C_6$–$C_{10}$)aryl($C_1$–$C_6$)aldoxy($C_6$–$C_{10}$)aryl, ($C_6$–$C_{10}$)aryl($C_1$–$C_6$)alkoxy ($C_2$–$C_9$)heteroaryl, ($C_2$–$C_9$)heteroaryloxy($C_1$–$C_6$)alkyl, ($C_2$–$C_9$)heteroaryloxy($C_6$–$C_{10}$)aryl, ($C_2$–$C_9$)heteroaryloxy($C_2$–$C_9$)heteroaryl, ($C_2$–$C_9$)heteroaryl($C_1$–$C_6$)alkoxy($C_1$–$C_6$)alkyl, ($C_2$–$C_9$)heteroaryl $(C_1-C_6)$alkoxy$(C_6-C_{10})$aryl or $(C_2-C_9)$heteroaryl $(C_1-C_6)$alkoxy$(C_2-C_9)$heteroaryl is optionally substituted on any of the ring carbon atoms capable of forming an additional bond by one or more substituents per ring independently selected from fluoro, chloro, bromo, $(C_1-C_6)$alkyl, $(C_1-C_6)$alkoxy, perfluoro$(C_1-C_3)$alkyl, perfluoro$(C_1-C_3)$alkoxy and $(C_6-C_{10})$aryloxy;

$R^1$ is hydrogen, $(C_1-C_6)$alkyl, $(C_6-C_{10})$aryl$(C_1-C_6)$alkyl, $(C_2-C_9)$heternryl$(C_1-C_6)$alkyl or a group of the formula

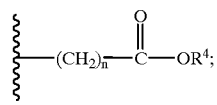

wherein $R^2$ and $R^3$ are independently hydrogen, $(C_1-C_6)$alkyl or $R^2$ and $R^3$ are taken together to form a three to seven membered cycloalkyl ring, a pyran-4-yl ring or a bicyclo ring of the formula

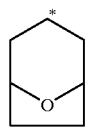

wherein the asterisk indicates the carbon atom common to $R^2$ and $R^3$;
and $R^4$ is $(C_1-C_6)$alkyl;
n is an integer from one to six; comprising:
a) reacting hydroxylamine, or a salt thereof, with a $((C_1-C_6)\text{alkyl})_3$silyl halide, preferably trimethylsilyl chloride, in the presence of a first base (preferably pyndine, 2,6-lutidine or diisopropylethylamine), in a solvent (preferably pyridine) to form an in situ $((C_1-C_6)\text{alkyl})_3$silylated hydroxylamine,
b) reaction of said in situ $((C_1-C_6)\text{alkyl})_3$silylated hydroxylamine with a compound of the formula

II

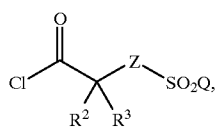

wherein $R^2$, $R^3$, Z and Q are as defined above, with a second base (preferably pyridine, 2,6-lutidine or diisopropylethylamine) to form a compound of the formula

VI

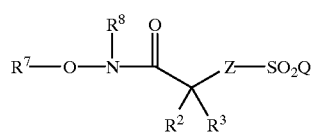

wherein $R^7$ is $((C_1-C_6)\text{alkyl})_3$—Si—, and $R^8$ is hydrogen or $((C_1-C_6)\text{alkyl})_3$—Si—, and
c) hydrolysis of said compound of formula VI with an acid.

The term "alkyl", as used herein, unless otherwise indicated, includes saturated monovalent hydrocarbon radicals having straight, branched or cyclic moieties or combinations thereof.

The term "alkoxy", as used herein, includes O-alkyl groups wherein "alkyl" is defined above.

The term "aryl", as used herein, unless otherwise indicated, includes an organic radical derived from an aromatic hydrocarbon by removal of one hydrogen, such as phenyl or naphthyl.

The term "heteroaryl", as used herein, unless otherwise indicated, includes an organic radical derived from an aromatic heterocyclic compound by removal of one hydrogen, such as pyridyl, furyl, pyroyl, thienyl, isothiazolyl, imidazolyl, benzimidazolyl, tetrazolyl, pyrazinyl, pyrimidyl, quinolyl, isoquinolyl, benzofuryl, isobenzofuryl, benzothienyl, pyrazolyl, indolyl, isoindolyl, purinyl, carbazolyl, isoxazolyl, thiazolyl, oxazolyl, benzthiazolyl or benzoxazolyl. Preferred heteroaryls include pyridyl, furyl, thienyl, isothiazolyl, pyrazinyl, pyrimidyl, pyrazolyl, isoxazolyl, thiazolyl or oxazolyl. Most preferred heteroaryls include pyridyl, furyl or thienyl.

The term "acyl", as used herein, unless otherwise indicated, includes a radical of the general formula R—(C=O)— wherein R is alkyl, alkoxy, aryl, arylalkyl or arylalkoxy and the terms, "alkyr" or "aryl" are as defined above.

The term "acyloxy", as used herein, includes O-acyl groups wherein "acyl" is defined above.

The compounds of formulae I–VI may have chiral centers and therefore exist in differernt diasteriomeric or enantiomeric forms. This invention relates to all optical isomers and stereoisomers of the compounds of formula I–VI and mixtures thereof.

Preferably, compounds of the formula I' exist as the exo isomer of the formula

I'

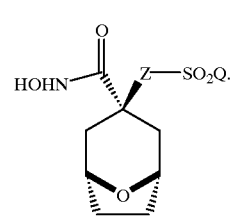

DETAILED DESCRIPTION

The following reaction Schemes illustrate the preparation of the compounds of the present invention. Unless otherwise indicated n, $R^1$, $R^2$, $R^3$, $R^4$, $R^5$, Q and Z in the reaction Schemes and the discussion that follow are defined as above.

SCHEME 1

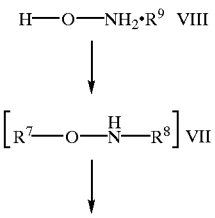

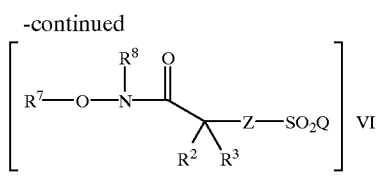

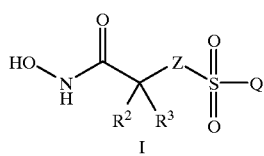

SCHEME 2

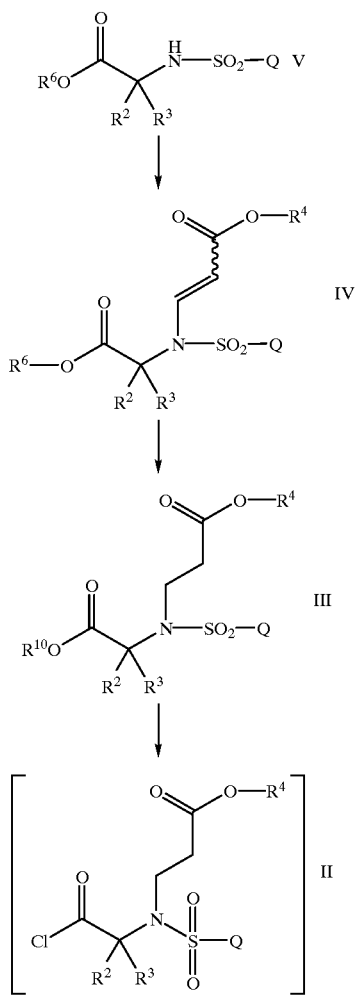

Scheme 1 refers to the preparation of matrix metalloproteinase compounds of formula I.

Referring to Scheme 1, compounds of formula I are prepared from a hydroxylamine of the formula VIII, wherein $R^9$ is hydrochloride, hydrosulfuric or $R^9$ is absent. Specifically, compounds of the formula VIII are reacted with a $((C_1-C_4)alkyl)_3$silyl halide in the presence of a base to form in situ a compound of the formula VII, wherein $R^7$ is $((C_1-C_6)alkyl)_3$—Si—, and $R^8$ is hydrogen or $((C_1-C_6)$ alkyl)$_3$—Si—. Suitable $((C_1-C_6)alkyl)_3$silyl halides include trimethylsilyl chloride, triethylsilyl chloride, trimethylsilyl iodide, triethylsilyl iodide, trimethylsilyl bromide, t-butyl dimethylsilyl chloride or triethylsilyl bromide, preferably trimethylsilyl chloride. Suitable bases include pyridine, 2,6-lutidine or diisopropylethylamine, preferably pyridine. The reaction is performed at a temperature of about 0° to about 22° C. (i.e., room temperature) for about 1 to about 12 hours, preferably about 1 hour.

The in situ formed compound of the formula VII is then reacted with a compound of formula II or the acid chloride of the compound of formula V, from Scheme 2, in the presence of a base to form in situ a compound of the formula VI, wherein $R^2$, $R^3$, $R^7$, $R^8$ and Q are as defined above and Z is >$NR^1$. Suitable bases include pyridine, 2,6-lutidine or diisopropylethylamine, preferably pyridine. The reaction is performed at a temperature of about 0° to about 22° C. (i.e., room temperature) for about 1 to about 12 hours, preferably about 1 hour.

The compound of formula VI is converted to a compound of formula I, wherein Z is >$NR^1$, by acid hydrolysis. Suitable acids include hydrochloric or sulfuric, preferably hydrochloric acid. The reaction is performed at a temperature of about 0° to about 22° C. (i.e., room temperature) for about 1 to about 12 hours, preferably about 1 hour.

Alternatively, compounds of the formula I, wherein Z is —(CH$_2$)— can be prepared by reacting a compound of the formula

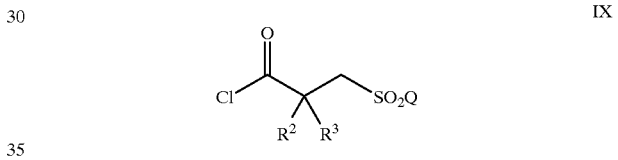

wherein $R^2$ and $R^3$ and Q are as defined above, with the compound of formula VII. Compounds of the formula IX can be prepared by the methods well known to those of ordinary skill in the art.

Scheme 2 refers to the preparation of compounds of formula II which are internediates used in the preparabon of compounds of the formula I, according to the methods of Scheme 1.

Referring to Scheme 2, compounds of formula II are prepared from compounds of the formula III, wherein $R^{10}$ is hydrogen, by reaction with oxalyl chloride or thionyl chloride, preferably oxalyl chloride, and a catalyst, preferably about 2% of N,N-dimethylformamide, in an inert solvent such as methylene chloride or toluene. The aforesaid reaction is performed at a temperature of about 0° C. (i.e., room temperature) to about 70° C., preferably about 20° C. to about 50° C., most preferably about 20° C. The aforesaid reaction period is about 1 to 7 hours, preferably about 2 hours.

Compounds of the formula III, wherein $R^{10}$ is hydrogen, can be prepared from compounds of the formula IV, wherein $R^6$ is optionally substituted benzyl, by reduction in a polar solvent. Suitable reducing agents include palladium catalyzed reductions such as hydrogen over palladium, hydrogen over palladium on carbon or palladium hydroxide on carbon, preferably hydrogen over palladium on carbon. Suitable solvents include tetrahydrofuran, methanol, ethanol and isopropanol and mixtures thereof, preferably ethanol. The aforesaid reaction is performed at a temperature of about 22° C. (i.e., room temperature) for a period of 1 to 7 days, preferably about 2 days.

Compounds of the formula III, wherein $R^{10}$ is other than hydrogen, such as a protonated amine (such as protonated primary amine, secondary amine or tertiary amine), alkali metal or alkaline earth metal, can be prepared from compounds of the formula III, wherein $R^{10}$ is hydrogen, by treatment with an aqueous or alkanolic solution containing an acceptable cation (e.g., sodium, potassium, dicyclohexylamine, calcium and magnesium, preferably dicyclohexylamine), and then evaporating the resulting solution to dryness, preferably under reduced pressure or filtering the precipitate, preferably the dicyclohexylamine salt precipate.

Compounds of the formula IV can be prepared from compounds of the formula V, wherein $R^6$ is optionally substituted benzyl, by Michael addition to a propiolate ester in the presence of a base in a polar solvent. Suitable propiolates are of the formula $H—C\equiv C—C—CO_2R^4$ wherein $R^4$ is $(C_1–C_6)$alkyl. Suitable bases include tetrabutylammonium fluoride, potassium carbonate, tertiary amines and cesium carbonate, preferably tetrabutylammonium fluoride. Suitable solvents include tetrahydrofuran, acetonitrile, tert-butanol, t-amyl alcohols and N,N-dimethylformamide, preferably tetrahydrofuran. The aforesaid reaction is performed at a temperature of about −10° C. to about 60° C., preferably ranging between 0° C. and about 22° C. (i.e., room temperature). The compounds of formula IV are obtained as mixtures of geometric isomers about the olefinic double bond; separation of the isomers is not necessary.

Compounds of the formula V wherein $R^2$ and $R^3$ are tetrahydropyran-4-yl or a bicyclc, ring of the formula

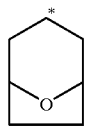

wherein the asterisk indicates the carbon atom common to $R_2$ and $R_3$ can be prepared according to methods analogous to those of Examples 3 and 4.

Compounds of the formula V, wherein $R^6$ is optionally substituted benzyl, can be prepared according to methods known in the art. Examples of such preparations include the following publications and applications. Matrix metalloproteinase inhibitors are well known in the literature. Specifically, PCT publication WO 96/33172 published Oct. 24, 1996, refers to cyclic arylsulfonylamino hydroxamic acids that are useful as MMP inhibitors. U.S. Pat. No. 5,672,615, PCT Publication WO 97/20824, PCT Publication WO 98/08825, PCT Publication WO 98/27069, and PCT Publication WO 98/34918, published August 13, 1998, entitled "Arylsulfonyl Hydroxamic Acid Derivatives" all refer to cyclic hydroxamic acids that are useful as MMP inhibitors. PCT Publications WO 96/27583 and WO 98/07697, published Mar. 7, 1996 and Feb. 26, 1998, respectively, refer to arylsulfonyl hydroxamic acids. PCT Publication WO 98/03516, published Jan. 29, 1998 refers to phosphinates with MMP activity. PCT Publication WO 98/34915, published Aug. 13, 1998, entitled "N-Hydroxy-β-Sulfonyl Propionamide Derivatives," refers to propionyl-hydroxamides as useful MMP inhibitors. PCT Publication WO 98/33768, published Aug. 6, 1998, entitled "Arylsulfonylamino Hydroxamic Acid Derivatives," refers to N-unsubstituted arylsulfonylamino hydroxamic acids. PCT Publication WO 98/30566, published Jul. 16, 1998, entitled "Cyclic Sulfone Derivatives," refers to cyclic sulfone hydroxamic acids as MMP inhibitors. U.S. Provisional Patent Application No. 60/55208, filed Aug. 8, 1997, refers to biaryl hydroxamic acids as MMP inhibitors. U.S. Provisional Patent Application Serial No. 60/55207, filed Aug. 8, 1997, entitled "Aryloxyarylsulfonylamino Hydroxamic Acid Derivatives," refers to aryloxyarylsulfonyl hydroxamic acids as MMP inhibitors. Each of the above referenced publications and applications is hereby incorporated by reference in its entirety.

The compounds of the formula I which are basic in nature are capable of forming a wide variety of different salts with various inorganic and organic acids. Although such salts must be pharmaceutically acceptable for administration to animals, it is often desirable in practice to initially isolate a compound of the formula I from the reaction mixture as al pharmaceutically unacceptable salt and then simply convert the latter back to the free bases compound by treatment with an alkaline reagent, and subsequently convert the free base to a pharmaceutically acceptable acid addition salt. The acid addition salts of the base compounds of this invention are readily prepared by treating the base compound with a substantially equivalent amount of the chosen mineral or organic acid in an aqueous solvent medium or in a suitable organic solvent such as methanol or ethanol. Upon careful evaporation of the solvent, the desired solid salt is obtained.

The acids which are used to prepare the pharmaceutically acceptable acid addition salts of the base compounds of this invention are those which form non-toxic acid addition salts, i.e., salts containing pharmacologically acceptable anions, such as hydrochloride, hydrobromide, hydroiodide, nitrate, sulfate or bisulfate, phosphate or acid phosphate, acetate, lactate, citrate or acid citrate, tartrate or bitartrate, succinate, maleate, fumarate, gluconaire, saccharate, benzoate, methanesulfonate and pamoate [ie., 1,1'-methylene-bis-(2-hydroxy-3-naphthoate)] salts.

Those compounds of the formula I which are also acidic in nature, are capable of forming base salts with various pharmacologically acceptable cations. Examples of such salts include the alkali metal or alkaline-earth metal salts and particularly, the sodium and potassium salts. These salts are all prepared by conventional techniques. The chemical bases which are used as reagents to prepare the pharmaceutically acceptable base salts of this invention are those which form non-toxic base salts with the herein described acidic compounds of formula I. These non-toxic base salts include those derived from such pharmacologically acceptable cations as sodium, potassium, calcium and magnesium, etc. These salts can easily be prepared by treating the corresponding acidic compounds with an aqueous solution containing the desired pharmacologically acceptable cations, and then evaporating the resulting solution to dryness, preferably under reduced pressure. Alternatively, they may also be prepared by mixing lower alkanolic solutions of the acidic compounds and the desired alkali metal alkoxide together, and then evaporating the resulting solution to dryness in the same manner as before. In either case, stoichiometric quantities of reagents are preferably employed in order to ensure completeness of reaction and maximum product yields.

The ability of the compounds of formula I or their pharmaceutically acceptable salts (hereinafter also referred to as the active compounds) to inhibit matrix metalloproteinases or the production of tumor necrosis factor (TNF) and, consequently, demonstrate their effectiveness for treating diseases characterized by matrix metalloproteinase or the production of tumor necrosis factor can be determined according to in vitro assay tests well known to those of ordinary skill in the art.

The following Examples illustrate the preparation of the compounds of the present invention. Melting points are uncorrected. NMR data are reported in parts per million (δ) and are referenced to the deuterium lock signal from the sample solvent (deuteriochloroform unless otherwise specified). Commercial reagents were utilized without further purification. THF refers to tetrahydrofuran. DMF refers to N,N-dimethylformamide. Chromatography refers to column chromatography performed using 32–63 mm silica gel and executed under nitrogen pressure (flash chromatography) conditions. Room or ambient temperature refers to 20–25° C. All non-aqueous reactions were run under a nitrogen atmosphere for convenience and to maximize yields. Concentration at reduced pressure means that a rotary evaporator was used.

EXAMPLE 1

3-[[4-(4-FLUOROPHENOXY) BENZENESULFONY]-(1-HYDROXYCARBAMOYL-CYCLOPENTYL)-AMINO]-PROPIONIC ACID

A) 1-[4-(4-Fluorophenoxy)benzenesulfonylamino] cyclopentanecarboxylic Acid Benzyl Ester To a mixture of 12.41 9 (0.032 mol) of 1-aminocyclopentanecarboxylic acid benzyl ester, toluene4-sulfonic acid salt, (can be prepared according to the methods described in U.S. Pat. No. 4,745,124) and 10.0 g (0.035 mol, 1.1 equivalents) of 4-(4-fluorophenoxy)benzenesulfonyl chloride in 113 mL of toluene was added 11.0 mL (0.079 mol, 2.5 equivalents) of triethylamine. The resulting mixture was stirred at ambient temperature overnight, washed with 2N hydrochloric acid (2×100 mL) and brine (100 mL), dried over sodium sulfate, and concentrated to 30 mL. Hexane, 149 mL, was added drop-wise over three hours giving a solid precipitate which was granulated at 0° C. for one hour and filtered yielding 12.59 g (85%) of 1-[4-(4-fluorophenoxy)benzenesulfonylamino]cyclopentane-carboxylic acid benzyl ester.

$^1$H NMR (CDCl$_3$) δ 7.78–7.82 (m, 2H), 7.30–7.39 (m, 5H), 7.06–7.12 (m, 2H), 6.99–7.04 (m, 2H), 6.93–6.97 (m, 2H), 5.15 (s, 1H), 5.02 (s, 2H), 2.04–2.13 (m, 2H), 1.92–1.98 (m, 2H), 1.62–1.69 (m, 4H).

A 4.0 g sample was granulated in a mixture of 4 mL of ethyl acetate and 40 mL of hexanes overnight giving 3.72 g (93% recovery) of 1-[4-(4-fluorophenoxy) benzenesulfonylamino]cyclopentane-carboxylic acid benzyl ester as light tan solids, mp 97.0–97.5° C.

B) 1-{(2-Ethoxycarbonylvinyl)-[4-(4-fluorophenoxy) benzenesulfonyl]amino}-cyclopentane-carboxylic Acid Benzyl Ester A solution of 25.0 g (532 mmol) of 1-[4-(4-fluorophenoxy)benzenesulfonylamino]cyclopentane-carboxylic acid benzyl ester and 10.8 mL (106 mmol, 2 equivalents) of ethyl propiolate in 200 mL of dry tetrahydrofuran at 1° C. was treated with 53.2 mL (53.2 mmol, 1 equivalent) of a solution of tetrabutylammonium fluoride in tetrahydrofuran (1M) over 45 minutes. The resulting solution was allowed to warm slowly to ambient temperature and stirred overnight, The tetrahydrofuran was displaced with toluene at reduced pressure, and the toluene solution was washed with water and brine, diluted to 600 mL with toluene, stirred with 90 g of silica gel for three hours, filtered, and concentrated to 25.14 g (83%) of 1-{(2-ethoxycarbonyivinyl)-[4-(4-fluorophenoxy) benzenesulfonyl]amino}-cyclopentanecarboxylic acid benzyl ester as an orangea oil. $^1$H NMR (CDCl$_3$) indicated a 1.5:1 translcis ratio.

Trans δ 7.74–7.78 (m, 2H), 7.72 (d, J=14 Hz, 1H), 7.26–7.36 (m, 5H), 6.96–7.12 (m, 4H), 6.78–6.84 (m, 2H), 5.44 (d, J=14 Hz, 1H), 5.11 (s, 2H), 4.12 (q, J=7.1 Hz, 2H), 2.08–2.43 (m, 4H), 1.63–1.80 (m, 4H), 1.24 (t, J=7.1 Hz, 3H). Cis δ 7.68–7.72 (m, 2H), 7.26–7.36 (m, 5H), 6.96–7.12 (m, 4H), 6.86–6.91 (m, 2H), 6.47 (d, J=8.1 Hz, 1H), 5.90 (d, J=8.1 Hz, 1H), 5.11 (s, 2H), 3.93 (q, J=7.2 Hz, 2H), 2.08–2.43 (m, 4H), 1.63–1.80 (m, 4H), 1.17 (t, J=7.2 Hz, 3H).

C) 1-{(2-Ethoxycarbonylethyl)-[4-(4-fluorophenoxy) benzenesulfonyl]amino}-cyclopentane-carboxylic Acid A solution of 2.50 g (4.4 mmol) of 1-{(2-ethoxycarbonylvinyl)-[4-(4-fluorophenoxy) benzenesulfonyl]amino}cyclopentanecarboxylic acid benzyl ester in 25 mL of ethanol was treated with 2.5 9 of 50% water wet 10% palladium on carbon catalyst and shaken under 53 psi of hydrogen for 21 hours. The catalyst was removed by filtration and washed with ethanol (4×25 mL). The filtrate and washings were combined and concentrated under vacuum to 1.74 g (82%) of crude 1-{(2-ethoxycarbonylethyl)-[4-(4-fluorophenoxy) benzenesulfonyl]amino}cyclopentanecarboxylic acid_ as a viscous oil.

$^1$H NMR (CDCl$_3$) δ7.78–7.82 (m, 2H), 6.94–7.09 (m, 6H), 4.09 (q, J=7.2 Hz, 2H), 3.56–3.60 (m, 2H), 2.75–2.79 (m, 2H), 2.33–2.39 (m, 2H), 1.93–2.03 (m, 2H), 1.69–1.76 (m, 2H), 1.56–1.63 (m, 2H), 1.22 (t, J=7.2 Hz, 3H).

D) 1-{(2-Ethoxycarbonylethyl)-[4-(4-fluorophenoxy) benzenesulfonyl]-amino}-cyclopentane-carboxylic Acid, Dicyclohexylaminium Salt A solution of 3.10 g (6.5 mmol) of crude 1-{(2-ethoxycarbonylethyl)-[4-(4-fluorophenoxy)-benzenesulfonyl]amino}cyclopentanecarboxylic acid in 30 mL of ethanol was treated with 1.28 mL (6.5 mmol, 1 equivalent) of dicyclohexylamine at ambient temperature producing solids within five minutes. This mixture was stirred at ambient temperatures overnight and then at 0° C. for five hours. White solids were isolated by filtration, washed with 10 mL of cold ethanol, and air dried giving 2.89 g (67%) of 1-{(2-ethoxycarbonylethyl)-[4-(4-fluorophenoxy)benzenesulfonyl] amino}cyclopentanecarboxylic acid, dicyclohexylaminium salt.

$^1$H NMR (CDCl$_3$) δ 7.86–7.91 (m, 2H), 6.99–7.09 (m, 4H), 6.906.94 (m, 2H), 5.3 (br s, 2H), 4.07 (q, J=7.1 Hz, 2H), 3.54–3.59 (m 2H), 2.88–2.95 (m, 4H), 2.31–2.38 (m, 2H), 1.95–2.22 (m, 6H), 1.68–1.77 (m, 6H), 1.53–1.60 (m, 4H), 1.40–1.50 (m, 4H), 1.21 (t, J=7.1 Hz, 3H), 1.14–1.22 (m, 6H). Mp 164.5–165.9° C.

E) 1-{(2-Ethoxycarbonylethyl)-[4-(4-fluorophenoxy) benzenesulfonyl]-amino}-cyclopentane-carboxylic Acid A solution of 3.0 g (4.5 mmol) of 1-{(2-ethoxycarbonylethyl)-[4-(4-fluorophenoxy)-benzenesulfonyl]amino}cyclopentanecarboxylic acid, dicyclohexylaminium salt in 30 mL of dichloromethane was treated with 30 mL of 2N hydrochloric acid at ambient temperature causing immediate precipitation of solids. This mixture was stirred at ambient temperature for three hours. The solids were filtered, the aqueous phase was extracted with dichloromethane, and the combined organic phases were washed with water, dried over sodium sulfate, and concentrated under vacuum to 2.2 g (100%) of 1-{(2-ethoxycarbonylethyl)-[4-(4-fluorophenoxy) benzenesulfonyl]amino}cyclopentanecarboxylic acid as a clear oil.

$^1$H NMR (DMSO-d$_6$) δ12.68 (bs, 1H), 7.76–7.80 (m, 2H), 7.25–7.31 (m, 2H), 7.16–7.21 (m, 2H), 7.03–7.08 (m, 2H), 4.01 (q, J=7.1 Hz, 2H), 3.48–3.54 (m, 2H), 2.64–2.70 (m, 2H), 2.13–2.21 (m, 2H), 1.90–1.98 (m, 2H), 1.52–1.59 (m, 4H), 1.14 (t, J=7.1 Hz, 3H).

F) 3-{(1-Chlorocarbonylcyclopentyl)-[4-(4-fluorophenoxy)benzenesulfonyl]-amino}-propionic Acid Ethyl Ester A solution of 7.26 g (15.1 mmol) of 1-{(2-ethoxycarbonylethyl)-[4-(4-fluorophenoxy)benzenesulfonyl]amino}cyclopentanecarboxylic acid in 73 mL of dichloromethane was treated with 1.4 mL (17 mmol, 1.1 equivalents) of oxalyl chloride and 0.02 mL (0.3 mmol, 0.02 equivalents) of dimethylformamide at ambient temperature, causing some bubbling, and stirred overnight. The resulting solution of 3-{(1-chlorocarbonylcyclopentyl)-[4-(4-fluorophenoxy)benzenesulfonyl]amino}propionic acid ethyl ester was used for the preparation of 3-[[4-(4-fluorophenoxy)benzenesulfonyl]-(1-hydroxycarbamoylcyclopentyl)-amino]propionic acid ethyl ester without isolation.

A similarly prepared solution of 3{(1-chlorocarbonylcyclopentyl)-[4-(4-fluorophenoxy)-benzenesulfonyl]amino}propionic acid ethyl ester was concentrated under vacuum to an oil.

$^1$H NMR (CDCl$_3$) δ 7.84–7.87 (m, 2H), 6.97–7.12 (m, 6H), 4.10 (q, J=7.2 Hz, 2H), 3.55–3.59 (m, 2H), 2.68–2.72 (m, 2H), 2.47–2.53 (m, 2H), 1.95–2.02 (m, 2H), 1.71–1.76 (m, 4H), 1.24 (t, J=7.2 Hz, 3H).

G) 3-[[4-(4-Fluorophenoxy)benzenesulfonyl]-(1-hydroxycarbamoylcyclo-pentyl)-amino]-propionic Acid Ethyl Ester A solution of 1.37 g (19.7 mmol, 1.3 equivalents) of hydroxylamine hydrochloride in 9.2 mL (114 mmol, 7.5 equivalents) of dry pyridine at 0° C. was treated with 5.8 mL (45 mmol, 3.0 equivalents) of trimethylsilyl chloride, causing white solids to precipitate, and allowedc to warm to ambient temperature overnight. This mixture was cooled to 0° C. and treated with a solution of 7.54 g (15.1 mmol) of 3-{(1-chlorocarbonylcyclopentyl)-[4-(4-fluorophenoxy)benzenesulfonyl]amino}propionic acid ethyl ester in 73 mL of dichloromethene, prepared as described above without isolation, causing an exotherm to 8° C. This mixture was stirred at 0° C. for 30 minutes and at ambient temperature for one hour before treating with 50 mL of 2N aqueous hydrochloric acid and stirring at ambient temperature for one hour. The aqueous phase was extracted with dichloromethane and the combined organic phases were washed with 2N aqueous hydrochloric acid (2×50 mL) and water (50 mL). This solution of 3-[[4-(4-fluorophenoxy)benzenesufonyl]-(1-hydroxycarbamoylcyclopentyl)amino]propionic acid ethyl ester in dichloromethane was used for the preparation of 3-[[4-(4-fluoro-phenoxy)benzenesulfonyl]-1-hydroxycarbamoylcyclopentyl)amino]propionic acid without isolation. An aliquot was concentrated to a foam.

$^1$H NMR (DMSO-d$_6$) δ 10.37 (s, 1H), 8.76 (s, 1H), 7.74–7.79 (m, 2H), 7.24–7.30 (m, 2H), 7.14–7.20 (m, 2H), 7.01–7.05 (m, 2H), 3.99 (q, J=7.1 Hz, 2H), 3.42–3.47 (m, 2H), 2.62–2.67 (m, 2H), 2.16–2.23 (m, 2H), 1.77–1.85 (m, 2H), 1.43–1.52 (m, 4H), 1.13 (t, J=7.1 Hz, 3H).

A similarly prepared solution was concentrated under vacuum to 6.71 9 (89%) of 3-[[4-(4-fluorophenoxy)benzenesulfonyl]-(1-hydroxycarbamoylcyclopentyl)amino]propionic acid ethyl ester as a hard dry foam.

H) 3-[[4(4-Fluorophenoxy)benzenesulfonyl]-1-hydroxycarbamoylcyclo-pentyl)-amino]-propionic Acid A solution of 7.48 g (15.1 mmol) of 3-[[4-(4-fluorophenoxy)benzenesulfonyl]-(1-hydroxycarbamoylcyclopentyl)amino]propionic acid ethyl ester in dichloromethane was concentrated by rotary evaporation with the addition of 75 mL of toluene. This solution was treated with 75 mL of water, cooled to 0° C., and treated with 6.05 g (151 mmol, 10 equivalents) of sodium hydroxide pellets over 10 minutes with vigorous stirring. This mixture was stirred for 15 minutes at 0° C. and warmed to ambient temperature over one hour. The aqueous phase was separated, diluted with 7.5 mL of tetrahydrofuran, cooled to 0° C., and treated with 33 mL of 6N aqueous hydrochloric acid over 20 minutes. This mixture was stirred with 75 mL of ethyl acetate at 0° C. to ambient temperature, and the ethyl acetate phase was separated and washed with water. The ethyl acetate solution was slowly treated with 150 mL of hexanes at ambient temperature causing solids to precipitate, and stirred overnight. Filtration yielded 5.01 g of 3-[[4-(4-fluorophenoxy)benzenesulfonyl]-1-hydroxycarbamoylcyclopentyl)amino]propionic acid as a white solid (71% yield from 1-{(2-ethoxycarbonylethyl)-[4-(4-fluorophenoxy)benzenesulfonyl]amino}cyclopentanecarboxylic acid).

$^1$H NMR (DMSO-d$_6$) δ 12.32 (s, 1H), 10.43 (s, 1H), 8.80 (s, 1H), 7.82 (d, J=8.6 Hz, 2H), 7.28–7.35 (m, 2H), 7.20–7.26 (m, 2H), 7.08 (d, J=8.9 Hz, 2H), 3.44–3.49 (m, 2H), 2.61–2.66 (m, 2H), 2.24–2.29 (m, 2H), 1.86–1.90 (m, 2H), 1.54–1.55 (m, 4H). Mp 162.9–163.5° C. (dec).

EXAMPLE 2

3-[[4-(4-Fluoro-phenoxy)-benzenesulfonyl]-(4-hydroxycarbamoyl-tetrahydro-pyran-4-yl)-amino]-propionic acid A) 4-[N-(Diphenylmethylene)amino]tetrahydropyran-4-carboxyilc acid benzyl ester To a suspension of sodium hydride (6.56 grams. 0.164 mole) in ethylene glycol dimethyl ether (150 mL) at 0° C. is added a solution of the N-(diphenylmethylene)glycine benzyl ester (0.07398 mole) in ethylene glycol dimethyl ether (50 mL) dropwise via addition funnel. A solution of 2-bromoethyl ether (23.21 grams, 0.090 mole) in ethylene glycol dimethyl ether (50 mL) is then added, in 10 mL portions over approximately 5 minutes, to the ethylene glycol dimethyl ether solution. The ice bath is removed and the reaction is stirred at room temperature for 16 hours. The mixture is diluted with diethyl ether and washed with water. The aqueous layer is extracted with diethyl ether. The combined organic extracts are washed with brine, dried over magnesium sulfate, and concentrated to afford crude product. Chromatography on silica gel eluting first with 4 L of 5% ethyl acetate/hexane followed by 4 liters of 10% ethyl acetate/hexane provides 4-[N-(diphenylmethylene)amino]tetrahydropyran-4-carboxylic acid benzyl ester as a clear yellow oil.

B) 4-Aminotetrahydropyran-4-carboxylic acid benzyl ester

To a solution of 4-[N-(diphenylmethylene)amino]tetrahydropyran-4-carboxylic acid benzyl ester (16.0 grams, 0.047 mole) in diethyl ether (120 mL) is added 1M aqueous hydrochloric acid solution (100 mL). The mixture is stirred vigorously at room temperature for 16 hours. The layers are separated and the aqueous layer washed with diethyl ether. The aqueous layer is brought to pH 10 with dilute aqueous ammonium hydroxide solution and extracted with dichloromethane. The organic extract is dried over sodium sulfate and concentrated to give 4-aminotetrahydropyran-4-carboxylic acid benzyl ester.

C) 4-[4-(4-Fluorophenoxy)benzenesulfonylamino] tetrahydropyran-4-carboxylic acid benzyl ester To a solution of 4-aminotetrahydropyran-4-carboxylic acid benzyl ester (0.0404 mole) in N,N-dimethylformamide (40 mL) is added triethylamine (5.94 mL, 0.043 mole). Solid 4-(4-fluorophenoxy)benzenesulfonyl chloride (12.165 grams, 0.0424 mole) is added to the abovte solution in portions. The resulting mixture is stirred at room temperature for 16 hours and then most of the solvent is removed by evaporation under vacuum. The residue was partitioned between saturated sodium bicarbonate solution and dichloromethane. The aqueous layer is separated and extracted with dichloromethane. The combined organic layers are washed with brine and dried over sodium sulfate. Evaporation of the solvent under vacuum provided crude 4-[4-(4-fluorophenoxy)benzenesulfonylamino]tetrahydropyran-4-carboxylic acid benzyl ester. Flash chromatography on silica gel eluting with 25% ethyl acetate/hexane followed by 50% ethyl acetate/hexane provided 4-[4-(4-fluorophenoxy) benzenesulfonylamino]tetrahydropyran-4-carboxylic acid benzyl ester.

D) 4-{(2-Ethoxycarbonyl-vinyl)-[4-(4-fluoro-phenoxy)-benzenesulfonyl]-amino}-tetrah ydro-pyran-4-carboxylic acid benzyl ester A solution of (53.2 mmol) of the product of the previous step and 10.8 mL (106 mmol, 2 equivalents) of ethyl propiolate in 200 mL of dry tetrahydrofuran at 1° C. is treated with 53.2 mL (53.2 mmol, 1 equivalent) of a solution of tetrabutylammonium fluoride in tetrahydrofuran (1M) over 45 minutes. The resulting solution is allowed to warm slowly to ambient temperature and stirred overnight. The tetrahydrofuran is displaced with toluene at reduced pressure, and the toluene solution is washed with water and brine, diluted to 600 mL with toluene, stirred with 90 g of silica gel for three hours, filtered, and concentrated to the title compound.

E) 4-{(2-Ethoxycarbonyl-ethyl)-[4-(4-fluoro-phenoxy)-benzenesulfonyl]-amino}-tetrah ydro-pyran-4-carboxylic acid A solution of (4.4 mmol) of the product of step D in 25 mL of ethanol is treated with 2.5 g of 50% water wet 10% palladium on carbon catalyst and shaken under 53 psi of hydrogen for 21 hours. The catalyst is removed by filtration and washed with ethanol (4×25 mL). The filtrate and washings are combined and concentrated under vacuum to crude product.

F) 3-{(4-Chlorocarbonyl-tetrahydro-pyran-4-yl)-[4-(4-fluoro-phenoxy)-benzenesulfonyl]-amino}-propionic acid ethyl ester A solution of (15.1 mmol) of the product from Step E in 73 mL of dichloromethane is treated with 1.4 mL (17 mmol, 1.1 equivalents) of oxalyl chloride and 0.02 mL (0.3 mmol, 0.02 equivalents) of dimethylformamide at ambient temperature, causing some bubbling, and is stirred overnight. The resulting solution of the title compound is used in the next step without isolation.

G) 3-[[4-(4-Fluoro-phenoxy)-benzenesulfonyl]-(4-hydroxycarbamoyl-tetrahydro-pyran-4-yl)-amino]-propionic acid ethyl ester A solution of (19.7 mmol, 1.3 equivalents) of hydroxylamine hydrochloride in 9.2 mL (114 mmol, 7.5 equivalents) of dry pyridine at 0 ° C. is treated with 5.8 mL (45 mmol, 3.0 equivalents) of trimethylsilyl chloride, causing white solids to precipitate. The mixture is allowed to warm to ambient temperature overnight This mixture is then cooled to 0° C. aind treated with a solution of (15.1 mmol) of the product from Step F in 73 mL of dichloromethane causing an exotherm to about 8° C. This mixture is stirred at 0° C. for 30 minutes and at ambient temperature for about one hour. The reaction is then treated with 50 mL of 2N aqueous hydrochloric acid and was stirred at ambient temperature for one hour. The aqueous phase is extracted with dichloromethane and the combined organic phases are washed with 2N aqueous hydrochloric acid (2×50 mL) and water (50 mL). This solution of the title compound in dichloromethane is used in the next step.

(H) 3-[[4-(4-Fluoro-phenoxy)-benzenesulfonyl]-(4-hydroxycarbamoyl-tetrahydro-pyran-4-yl)-amino]-propionic acid A solution of (15.1 mmol) of the product from Step G in dichloromethane is concentrated by rotary evaporation with the addition of 75 mL of toluene. This solution is treated with 75 mL of water, cooled to 0° C., and treated with 6.05 g (151 mmol, 10 equivalents) of sodium hydroxide pellets over 10 minutes with vigorous stirring. This mixture is stirred for 15 minutes at 0° C. and warmed to ambient temperature over one hour. The aqueous phase is separated, diluted with 7.5 mL of tetrahydrofuran, cooled to 0° C., and treated with 33 mL of 6N aqueous hydrochloric acid over 20 minutes. This mixture is stirred with 75 mL of ethyl acetate at 0° C. to ambient temperature, and the ethyl acetate phase is separated and washed with water. The ethyl acetate solution was concentrated to yield the title compound.

EXAMPLE 3

3-[[4-(4-Fluoro-phenoxy)-benzenesulfonyl]-(3-hydroxycarbamoyl-8-oxa-bicyclo[3.2.1]oct-3-yl)-amino]-propionic acid A) 3-(Benzhydrylideneamino)-8-oxabicyclo[3.2.1]octane-3-carboxylic acid benzyl ester To a suspension of sodium hydride (0.41 grams, 17.1 mmole) in N,N-dimethylformamide (50 mL) at 0° C. is added dropwise a solution of N-diphenylmethylene glycine benzyl ester (7.8 mmole) in N,N-dimethylformamide (50 mL). After stirring for 30 minutes at room temperature, a solution of cis-2,5-bis(hydroxymethyl)-tetrahydrofuran ditosylate (4.1 grams, 9.3 mmole,)(prepared by literature methods such as those described in JOC, 47, 2429–2435 (1982)) in N,N-dimethylformamide (50 mL) is added dropwise. The reaction mixture is gradually heated to 100° C. in an oil bath and stirred at this temperature overnight. The solvent is evaporated under vacuum and the residue is taken up in water and extracted twice with diethyl ether. The combined organic extracts are washed with brine, dried over magnesium sulfate and concentrated to a crude product.

B) 3-Amino-8oxabicyclo[3.2.1]octane-3-carboxylic acid benzyl ester hydrochloride A two-phase mixture of 3-(benzhydrylideneamino)-8-oxabicyclo[3.2.1]octane-3-carboxylic acid benzyl ester (3.9 mmole) in aqueous 1N hydrochloric acid solution (100 mL.) and diethyl ether (100 mL) is stirred at room temperature overnight. The aqueous layer ifs concentrated to provide the title compound.

C) 3-exo-[4-(4-Fluorophenoxy)benzenesulfonylamino]-8-oxabicyclo[3.2.1]-octane-3-carboxylic acid benzyl ester A solution of 3-amino-8-oxabicyclo[3.2.1]octane-3-carboxylic acid benzyl ester hydrochloride (2.9 mmole), 4-(4-fluorophenoxy)benzenesulfonylchloride (923 mg, 3.2 mmole) and triethylamine (0.9 mL, 6.5 mmole) in N,N-dimethylformamide (45 mL) is stirred at room temperature overnight. The solvent is removed under vacuum and the residue is taken up in saturated aqueous sodium bicarbonate solution. After extracting twice with methylene chloride, the combined organic layers are washed with brine, dried over magnesium sulfate and concentrated to a brown oil. The title compound is isolated by chromatography on silica using 1% methanol in methylene chloride as eluant.

D) 3-{(2-Ethoxycarbonyl-vinyl)-[4-(4-fluoro-phenoxy)-benzenesulfonyl]-amino}-8-oxa-bicyclo[3.2.1]octane-3-carboxylic acid benzyl ester A solution of (53.2 mmol) of the product of the previous step and 10.8 mL (106 mmol, 2 equivalents) of ethyl propiolate in 200 mL of dry tetrahydrofuran at 1° C. is treated with 53.2 mL (53.2 mmol, 1 equivalent) of a solution of tetrabutylammonium fluoride in tetrahydrofuran (1M) over 45 minutes. The resulting solution is allowed to warm slowly to ambient temperature and stirred overnight. The tetrahydrofuran is displaced with toluene at reduced pressure, and the toluene solution is washed with water and brine, diluted to 600 mL with toluene, stirred with 90 g of silica gel for three hours, filtered, and concentrated to the title compound.

E) 3-{(2-Ethoxycarbonyl-ethyl)-[4-(4-fluoro-phenoxy)-benzenesulfonyl]-amino}-8-oxa-bicyclo[3.2.1]octane-3-carboxylic acid A solution of (4.4 mmol) of the product of step D in 25 mL of ethanol is treated with 2.5 g of 50% water wet 10% palladium on carbon catalyst and shaken under 53 psi olF hydrogen for 48 hours. The catalyst is removed by filtration and washed with ethanol (4×25mL). The filtrate and washings are combined and concentrated under vacuum to crude product.

F) 3{(3Chlorocarbonyl-8-oxa-bicyclo[3.2.1]oct-3-yl)-[4-(4-fluoro-phenoxy)-benzene sulfonyl]-amino}-propionic acid ethyl ester A solution of (15.1 mmol) of the product from Step E in 73 mL of dichloromethane is treated with 1.4 mL (17 mmol, 1.1 equivalents) of oxalyl chloride and 0.02 mL (0.3 mmol, 0.02 equivalents) of dimethylformamide at ambient temperature, causing some bubbling, and is stirred overnight. The resulting solution of the title compound is used in the next step without isolation.

G) 3-[[4-(4-Fluoro-phenoxy)-benzenesulfonyl]-(3-hydroxycarbamoyl-oxa-bicyclo[3.2.1]oct-3-yl)-amino]-propionic acid ethyl ester A solution of (19.7 mmol, 1.3 equivalents) of hydroxylamine hydrochloride in 9.2 mL (114 mmol, 7.5 equivalents) of dry pyridine at 0 ° C. is treated with 5.8 mL (45 mmol, 3.0 equivalents) of trimethylsilyl chloride, causing white solids to precipitate. The mixture is allowed to warm to ambient temperature overnight. This mixture is then cooled to 0° C. and treated with a solution of (15.1 mmol) of the product from Step F in 73 mL of dichloromethane causing an exotherm to about 8° C. This mixture is stirred at 0° C. for 30 minutes and at ambient temperature for about one hour. The reaction is then treated with 50 mL of 2N aqueous hydrochloric acid and was stirred at ambient temperature for one hour. The aqueous phase is extracted with dichloromethane and the combined organic phases are washed with 2N aqueous hydrochloric acid (2×50 mL) and water (50 mL). This solution of the title compound in dichloromethane is used in the next step.

(H) 3-[[4-(4-Fluoro-phenoxy)-benzenesulfonyl]-(3-hydroxycarbamoyl-8-oxa-bicyclo[3.2.1]oct-3-yl)-amino]-propionic acid A solution of (15.1 mmol) of the product from Step G in dichloromethane is concentrated by rotary evaporation with the addition of 75 mL of toluene. This solution is treated with 75 mL of water, cooled to 0° C., and treated with 6.05 g (151 mmol, 10 equivalents) of sodium hydroxide pellets over 10 minutes with vigorous stirring. This mixture is stirred for 15 minutes at 0° C. and warmed to ambient temperature over one hour. The aqueous phase is separated, diluted with 7.5 mL of tetrahydrofuran, cooled to 0° C., and treated with 33 mL of 6N aqueous hydrochloric acid over 20 minutes. This mixture is stirred with 75 mL of ethyl acetate at 0° C. to ambient temperature, and the ethyl acetate phase is separated and washed with water. The ethyl acetate solution was concentrated to yield the title compound.

EXAMPLE 4

3-exo-[4-(4-Fluorophenoxy) benzenesulfonylmethyl]-8-oxabicyclo-[3.2.1]-octane-3-carboxylic acid hydroxyamide A) 8-Oxabicyclo[3.2.1]octane-3,3-dicarboxylic acid diethyl ester Sodium hydride (2.28 grams, 95 mmole) is added in portions to a stirred solution of diethyl malonate (15 mL, 99 mmole) in N,N-dimethylformamide (400 mL). The mixture is stirred for 45 minutes at which time evolution of hydrogen is complete. A solution of cis-2,5-bis(hydroxymethyl) tetrahydrofuran ditosylate (19.0 grams, 43 mmole) in N,N-dimethylformamide (400 mL) is then added dropwise. The mixture is heated in an oil bath at 140° C. overnight. After cooling to room temperature, the mixture was quenched by addition of saturated aqueous ammonium chloride solution and concentrated under vacuum. The residual oil is taken up in water and extracted with diethyl ether. The organic extract is washed with water and brine, dried over magnesium sulfate and concentrated to an oil.

B) 3-exo-Hydroxymethyl-8-oxabicyclo[3.2.1]octane-3-carboxylic acid ethyl ester

A 1.2 M solution of diisobutylaluminum hydride in toluene (75 mmole) is added dropwise to a solution of 8-oxabicyclo[3.2.1]octane-3,3-dicarboxylic acid diethyl ester (30 mmole) in toluene (80 mL) at −40° C. The mixture is allowed to warm to 0° C. while stirring for a period of 3 hours. It is then cooled to −15° C. and ethanol (8 mL) is added slowly while maintaining this temperature. After stirring at −15° C. for 1 hour, sodium borohydride (1.1 grams, 30 mmole) is added. The mixture was stirred at room temperature overnight and was quenched by dropwise addition of saturated aqueous sodium sulfate solution. Ethyl acetate was added and, after stirring for 20 minutes, the insoluble material was removed by filtration through Celite™. The filtrate was washed with brine, dried over magnesium sulfate and concentrated to afford the title compound as a clear oil.

C) 3-exo-Hydroxymethyl-8-oxabicyclo[3.2.1]octane-3-carboxylic acid

Lithium hydroxide hydrate (59.5 mmole) is added to a solution of 3-exo-hydroxymethyl-8-oxabicyclo[3.2.1] octane-3-carboxylic acid ethyll ester (23.8 mmole) in a mixture of methanol (25 mL), tetrahydrofuran (25 mL) and water (2.5 mL). The mixture is heated at reflux overnight, cooled and quenched by addition of Amberlite IR-120™ ion exchange resin. After stirring for 20 minutes, the resin is removed by filtration, washing with tetrahydrofuran. Evaporation of the solvents and trituration of the residue with diethyl ether afforded the title compound.

D) 3',8-Dioxaspiro[bicyclo[3.2.1]octane-3.1'-cyclobutane]-2'-one

Benzenesulfonylchlodde (13.5 mmole) is added dropwise to a solution of 3-exo-hydroxymethyl-8-oxabicyclo[3.2.1] octane-3-carboxylic acid (12.3 mmole), triethylamine (24.7 mmole) and 4-dimethylaminopyridine (2.5 mmole) in methylene chloride (50 mL) at 0° C. The mixture was stirred at 0° C. for 1 hour, diluted with methylene chloride and washed with aqueous 1N hydrochloric acid solution, saturated aqueous sodium bicarbonate solution and brine. After drying over magnesium sulfate, the solvent was evaporated to provide the title compound.

E) 3-exo-[4-(4-Fluorophenoxy)phenylsulfanylmethyl]-8-oxabicyclo[3.2.1]octane-3-carboxylic acid A solution of 4-(4-fluorophenoxy)thiophenol (10 mmole) in tetrahydrofuran (10 mL) is added dropwise to a slurry of sodium hydride (11.3 mmole) in tetrahydrofuran (20 mL) at −10° C. The mixture is allowed to warm to room temperature while stirring for 30 minutes. After cooling again to −10° C., a solution of 3',8-dioxaspiro[bicyclo[3.2.1]octane-3,1'-cyclobutane]-2'one (10 mmole) in tetrahydrofuran (20 mL) is added dropwise. The cooling bath was removed and stirring is continued at room temperature for 2 hours after which the mixture was quenched with aqueous 1N hydrochloric acid solution and extracted twice with methylene chloride. The combined organic extracts were washed with water and brine, dried over magnesium sulfate and concentrated to a solid.

F) 3-[4-(4-Fluoro-phenoxy)-phenylsulfanylmethyl]-8-oxa-bicyclo[3.2.1]octane-3-carbonyl chloride A solution of (15.1 mmol) of the product from Step E in 73 mL of dichloromethane is treated with 1.4 mL (17 mmol, 1.1 equivalents) of oxalyl chloride and 0.02 mL (0.3 mmol, 0.02 equivalents) of dimethylformamide at ambient temperature, causing some bubbling, and is stirred overnight. The resulting solution of the title compound is used in the next step without isolation.

G) 3-[4-(4-Fluoro-phenoxy)-phenylsulfanylmethyl]-8-oxa-bicyclo[3.2.1]octane-3-carboxylic acid hydroxyamide A solution of (19.7 mmol, 1.3 equivalents) of hydroxylamine hydrochloride in 9.2 mL (114 mmol, 7.5 equivalents) of dry pyridine at 0° C. is treated with 5.8 mL (45 mmol, 3.0 equivalents) of trimethylsilyl chloride, causing white solids to precipitate. The mixture is allowed to warm to ambient temperature overnight. This mixture is then cooled to 0° C. and treated with a solution of (15.1 mmol) of the product from Step F in 73 mL of dichloromethane causing an exotherm to about 8° C. This mixture is stirred at 0° C. for 30 minutes and at ambient temperature for about one hour. The reaction is then treated with 50 mL of 2N aqueous hydrochloric acid and is stirred at ambient temperature for one hour. The aqueous phase is extracted with dichloromethane and the combined organic phases are washed with 2N aqueous hydrochloric acid (2×50 mL) and water (50 mL). The organic phase is then concentrated to yield the title compound.

(H) 3-[4-(4-Fluoro-phenoxy)-benzenesulfonylmethyl]-8-oxa-bicyclo[3.2.1]octane-3-carboxylic acid hydroxyamide Oxone™ (8.63 mmole) is added to a solution of the product from the previous step, (3.63 mmole) in a mixture of water (30 mL), methanol (40 mL) and tetrahydrofuran (12 mL). The resulting mixture is stirred at room temperature overnight, diluted with water and extracted twice with ethyl acetate. The combined organic extracts are washed with brine, dried over magnesium sulfate and concentrated to form the title compound.

EXAMPLE 5

4-[4-(4-Fluoro-phonoxy)-benzenesulfonylamino]-tetrahydro-pyran-4-carboxylic acid hydroxyamide A) 4-[N-(Diphenylmethylene)amino]tetrahydropyran-4-carboxylic acid benzyl ester To a suspension of sodium hydride (6.56 grams. 0.164 mole) in ethylene glycol dimethyl ether (150 mL) at 0° C. is added a solution of the N-(diphenylmethylene)glycine benzyl ester (0.07398 mole) in ethylene glycol dimethyl ether (50 mL) dropwise via addition funnel. A solution of 2-bromoethyl ether (23.21 grams, 0.090 mole) in ethylene glycol dimethyl ether (50 mL) is then added, in 10 mL portions over approximately 5 minutes, to the ethylene glycol dimethyl ether solution. The ice bath is removed and the reaction is stirred at room temperature for 16 hours. The mixture is diluted with diethyl ether and washed with water. The aqueous layer is extracted with diethyl ether. The combined organic extracts are washed with brine, dried over magnesium sulfate, and concentrated to afford crude product. Chromatography on silica gel eluting first with 4 L of 5% ethyl acetate/hexane followed by 4 liters of 10% ethyl acetate/hexane provides 4-[N-(diphenylmethylene)amino] tetrahydropyran-4-carboxylic acid benzyl ester as a clear yellow oil.

B) 4-Aminotetrahydropyran-4-carboxylic acid benzyl ester

To a solution of 4-[N-(diphenylmethylene)amino] tetrahydropyran-4-carboxylic acid benzyl ester (16.0 grams, 0.047 mole) in diethyl ether (120 mL) is added 1M aqueous hydrochloric acid solution (100 mL). The mixture is stirred vigorously at room temperature for 16 hours. The layers are separated and the aqueous layer washed with diethyl ether. The aqueous layer is brought to pH 10 with dilute aqueous ammonium hydroxide solution and extracted with dichloromethane. The organic extract is dried over sodium sulfate and concentrated to give 4-aminotetrahydropyran-4-carboxylic acid benzyl ester.

C) 4-[4-(4-Fluorophenoxy)benzenesulfonylamino] tetrahydropyran-4-carboxylic acid benzyl ester To a solution of 4-aminotetrahydropyran-4-carboxylic acid benzyl ester (0.0404 mole) in N,N-dimethylformamide (40 mL) is added triethylamine (5.94 mL, 0.043 mole). Solid 4-(4-fluorophenoxy)benzenesulfonyl chloride (12.165 grams, 0.0424 mole) is added to the above solution in portions. The resulting mixture is stirred at room temperature for 16 hours and then most of the solvent is removed by evaporation under vacuum. The residue was partitioned between saturated sodium bicarbonate solution and dichloromethane. The aqueous layer is separated and extracted with dichloromethane. The combined organic layers are washed with brine and dried over sodium sulfate. Evaporation of the solvent under vacuum provided crude 4-[4-(4-fluorophenoxy)benzenesulfonylamino]tetrahydropyran-4-carboxylic acid benzyl ester. Flash chromatography on silica gel eluting with 25% ethyl acetate/hexane followed by 50% ethyl acetate/hexane provided 4-[4-(4-fluorophenoxy) benzenesulfonylamino]tetrahydropyran-4-carboxylic acid benzyl ester.

D) 4-{(2-Ethoxycarbonyl-vinyl)-[4-(4-fluoro-phenoxy)-benzenesulfonyl]-amino}-tetrahydro-pyran-4-carboxylic acid benzyl ester A solution of (53.2 mmol) of the product of the previous step and 10.8 mL (106 mmol, 2 equivalents) of ethyl propiolate in 200 mL of dry tetrahydrofuran at 1° C. is treated with 53.2 mL (53.2 mmol, 1 equivalent) of a solution of tetrabutylammonium fluoride in tetrahydrofuran (1M) over 45 minutes. The resulting solution is allowed to warm slowly to ambient temperature and stirred overnight. The tetrahydrofuran is displaced with toluene at reduced pressure, and the toluene solution is washed with water and brine, diluted to 600 mL with toluene, stirred with 90 g of silica gel for three hours, filtered, and concentrated to the title compound.

E) 4-[4-(4-Fluoro-phenoxy)-benzenesulfonylamino]-tetrahydro-pyran-4-carbonyl chloride A solution of 4.40 kg (11.13 mol) of 4-[4-(4-fluoro-phenoxy)-benzenesulfonylamino]-tetrahydro-pyran-4-carboxylic acid__ in 40 L of dichloromethane was treated with 19 mL of dimethylformamide and 1.075 L (12.32 mol, 1.1 equivalents) of oxalyl chloride at ambient temperature and was stirred for 16 hours. The resulting solution of the title compound was used in Step F without isolation.

F) 4-[4-(4-Fluoro-phenoxy)-benzenesulfonylamino]-tetrahydro-pyran-4-carboxylic acid hydroxyamide A solution of 1.160 kg (16.69 mol, 1.5 equivalents) of hydroxylamine hydrochloride in 6.8 L (84.08 mol, 7.5 equivalents) of pyridine at 0 to 10° C. was treated with 2.8 L (22.06 mol, 2.0 equivalents) of trimethylsilyl chloride, causing white solids to precipitate. This mixture was stirred for 4 hours at 0 to 2° C. before treatment with a solution of the Step E product in dichloromethane causing an exotherm. The reaction mixture was stirred for 1 hour at 0 to 2° C. and then 1.5 hours at 20° C. The reaction mixture was then treated with 132 L of 2N aqueous hydrochloric acid and was stirred at ambient temperature for one hour. The aqueous phase was extracted with ethyl acetate (3 times 100 L) and the combined organic phases were washed with water (2 times 130 L) and concentrated to 17 L. The resulting suspension was stirred at 0° C. for 3 hours and filtered giving 4.068 kg (89%) of the title compound as an off white solid.

What is claimed is:

1. A process for preparing a compound of the formula

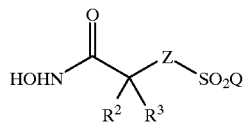

I $Z$ is $>CH_2$ or $>NR^1$;

$Q$ is $(C_1-C_6)$alkyl, $(C_6-C_{10})$aryl, $(C_2-C_9)$heteroaryl, $(C_6-C_{10})$aryloxy$(C_1-C_6)$alkyl, $(C_6-C_{10})$aryloxy$(C_6-C_{10})$aryl, $(C_6-C_{10})$aryloxy$(C_2-C_9)$heteroaryl, $(C_6-C_{10})$aryl$(C_1-C_6)$alkyl, $(C_6-C_{10})$aryl$(C_6-C_{10})$aryl, $(C_6-C_{10})$aryl$(C_2-C_9)$heteroaryl, $(C_6-C_{10})$aryl$(C_6-C_{10})$aryl$(C_1-C_6)$alkyl, $(C_6-C_{10})$aryl$(C_6-C_{10})$aryl$(C_6-C_{10})$aryl, $(C_6-C_{10})$aryl$(C_6-C_{10})$aryl$(C_2-C_9)$heteroaryl, $(C_2-C_9)$heteroaryl$(C_1-C_6)$alkyl, $(C_2-C_9)$heteroaryl$(C_6-C_{10})$aryl, $(C_2-C_9)$heteroaryl$(C_2-C_9)$heteroaryl, $(C_6-C_{10})$aryl$(C_1-C_6)$alkoxy$(C_1-C_6)$alkyl, $(C_6-C_{10})$aryl$(C_1-C_6)$alkoxy$(C_6-C_{10})$aryl, $(C_6-C_{10})$aryl$(C_1-C_6)$alkoxy$(C_2-C_9)$heteroaryl, $(C_2-C_9)$heteroaryloxy$(C_6-C_{10})$aryl, $(C_2-C_9)$heteroaryloxy$(C_2-C_9)$heteroaryl, $(C_2-C_9)$heteroaryl$(C_1-C_6)$alkoxy$(C_1-C_6)$alkyl, $(C_2-C_9)$heteroaryl$(C_1-C_6)$alkoxy$(C_6-C_{10})$aryl or $(C_2-C_9)$heteroaryl$(C_1-C_6)$alkoxy$(C_2-C_9)$heteroaryl;

wherein each $(C_6-C_{10})$aryl or $(C_2-C_9)$heteroaryl moieties of said $(C_6-C_{10})$aryl, $(C_2-C_9)$heteroaryl, $(C_6-C_{10})$aryloxy$(C_1-C_6)$alkyl, $(C_6-C_{10})$aryloxy$(C_6-C_{10})$aryl, $(C_6-C_{10})$aryloxy$(C_2-C_9)$heteroaryl, $(C_6-C_{10})$aryl$(C_1-C_6)$alkyl, $(C_6-C_{10})$aryl$(C_6-C_{10})$aryl, $(C_6-C_{10})$aryl$(C_2-C_9)$heteroaryl, $(C_6-C_{10})$aryl$(C_6-C_{10})$aryl$(C_1-C_6)$alkyl, $(C_6-C_{10})$aryl$(C_6-C_{10})$aryl$(C_6-C_{10})$aryl, $(C_6-C_{10})$aryl$(C_6-C_{10})$aryl$(C_2-C_9)$heteroaryl, $(C_2-C_9)$heteroaryl$(C_1-C_6)$alkyl, $(C_2-C_9)$heteroaryl$(C_6-C_{10})$aryl, $(C_2-C_9)$heteroaryl$(C_2-C_9)$heteroaryl, $(C_6-C_{10})$aryl$(C_1-C_6)$alkoxy$(C_1-C_6)$alkyl, $(C_6-C_{10})$aryl$(C_1-C_6)$alkoxy$(C_6-C_{10})$aryl, $(C_6-C_{10})$aryl$(C_1-C_6)$alkoxy$(C_2-C_9)$heteroaryl, $(C_2-C_9)$heteroaryloxy$(C_1-C_6)$alkyl, $(C_2-C_9)$heteroaryloxy$(C_6-C_{10})$aryl, $(C_2-C_9)$heteroaryloxy$(C_2-C_9)$heteroaryl, $(C_2-C_9)$heteroaryl$(C_1-C_6)$alkoxy$(C_1-C_6)$alkyl, $(C_2-C_9)$heteroaryl$(C_1-C_6)$alkoxy$(C_6-C_{10})$aryl or $(C_2-C_9)$heteroaryl$(C_1-C_6)$alkoxy$(C_2-C_9)$heteroaryl is optionally substituted on any of the ring carbon atoms capable of forming an additional bond by one or more substituents per ring independently selected from fluoro, chloro, bromo, $(C_1-C_6)$alkyl, $(C_1-C_6)$alkoxy, perfluoro$(C_1-C_3)$alkyl, perfluoro$(C_1-C_3)$alkoxy and $(C_6-C_{10})$aryloxy;

$R^1$ is hydrogen, $(C_1-C_6)$alkyl, $(C_6-C_{10})$aryl$(C_1-C_6)$alkyl, $(C_2-C_9)$heteroaryl$(C_1-C_6)$alkyl group of the formula

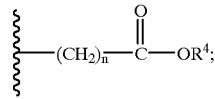

wherein $R^2$ and $R^3$ are independently hydrogen, $(C_1-C_6)$alkyl or $R^2$ and $R^3$ are taken together to form a three to seven membered cycloalkyl ring, a pyran-4-yl ring or a bicyclo ring of the formula

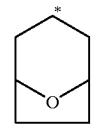

wherein the asterisk indicates the carbon atom common to $R^2$ and $R^3$;

and $R_4$ is $(C_1-C_6)$alkyl;

$n$ is an integer from one to six; comprising:

a) reacting hydroxylamine, or a salt thereof, with a $((C_1-C_6)$alkyl$)_3$silyl halide in the presence of a first base, to form an in situ $((C_1-C_6)$alkyl$)_3$silylated hydroxylamine, b) reaction of said in situ $((C_1-C_6)$alkyl$)_3$silylated hydroxylamine with a compound of the formula

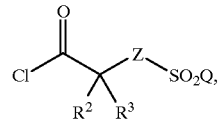

II wherein $R^2$, $R^3$, $Z$ and $Q$ are as defined above, with a second base to form a compound of the formula

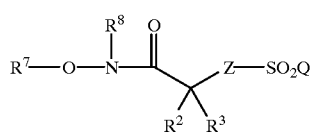

VI wherein $R^7$ is $((C_1-C_6)$alkyl$)_3$—Si—, and $R^8$ is hydrogen or $((C_1-C_6)$alkyl$)_3$—Si—; and c) hydrolysis of said compound of formula VI with an acid.

2. A process according to claim 1, wherein said first base is pyridine, 2,6-lufidirie or diisopropylethylamine.

3. A process according to claim 1, wherein said first base is pyridine.

4. A process according to claim 1, wherein said $((C_1-C_6)$alkyl$)_3$silyl halide is trimethyl silyl chloride.

5. A process according to claim 1, wherein said second base is pyridine, 2,6-lutidine or diisopropylethylamine.

6. A process according to claim 1, wherein said second base is pyridine.

7. A process according to claim 1, wherein said solvent is pyridine.

* * * * *